(12) United States Patent
Harding et al.

(10) Patent No.: US 11,660,113 B2
(45) Date of Patent: May 30, 2023

(54) MULTI-DIAMETER CANNULA

(71) Applicant: Becton, Dickinson and Company, Franklin Lakes, NJ (US)

(72) Inventors: Weston F. Harding, Lehi, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 239 days.

(21) Appl. No.: 17/131,370

(22) Filed: Dec. 22, 2020

(65) Prior Publication Data

US 2021/0106356 A1 Apr. 15, 2021

Related U.S. Application Data

(63) Continuation of application No. 15/461,363, filed on Mar. 16, 2017, now Pat. No. 10,898,223.

(60) Provisional application No. 62/314,261, filed on Mar. 28, 2016.

(51) Int. Cl.
  *A61B 17/34* (2006.01)
  *A61M 25/06* (2006.01)
  *A61M 5/32* (2006.01)

(52) U.S. Cl.
  CPC ...... *A61B 17/3421* (2013.01); *A61B 17/3415* (2013.01); *A61M 5/329* (2013.01); *A61M 25/065* (2013.01); *A61M 25/0631* (2013.01); *A61B 2017/3433* (2013.01)

(58) Field of Classification Search
  CPC .......... A61B 2017/3433; A61M 5/329; A61M 25/0023; A61M 5/50; A61M 5/1582
  See application file for complete search history.

(56) References Cited

U.S. PATENT DOCUMENTS

| | | |
|---|---|---|
| 3,540,447 A | 11/1970 | Howe |
| 4,160,450 A | 7/1979 | Doherty |
| 4,445,893 A | 5/1984 | Bodicky |
| 4,973,313 A | 11/1990 | Katsaros et al. |
| 5,514,107 A | 5/1996 | Haber et al. |
| D378,405 S | 3/1997 | Musgrave et al. |
| 5,676,656 A | 10/1997 | Brimhall |
| 5,728,135 A | 3/1998 | Bregen et al. |
| 5,772,636 A | 6/1998 | Brimhall et al. |
| D458,994 S | 6/2002 | Cindrich |
| 7,722,569 B2 | 5/2010 | Soderholm et al. |
| 8,551,051 B2 | 10/2013 | Salto et al. |

(Continued)

FOREIGN PATENT DOCUMENTS

| | | |
|---|---|---|
| CA | 2914701 | 12/2014 |
| CA | 2919785 | 2/2015 |

(Continued)

*Primary Examiner* — Deanna K Hall
(74) *Attorney, Agent, or Firm* — Kirton McConkie; Whitney Blair; Kevin Stinger

(57) ABSTRACT

A catheter assembly may include a cannula. The cannula may include a distal tip, an elongated tubular shaft, and an inner lumen formed by the elongated tubular shaft. A first portion of the elongated tubular shaft may have a first outer diameter. The first portion may be proximate the distal tip. A second portion of the elongated tubular shaft may have a second outer diameter. The second outer diameter may be greater than the first outer diameter. The catheter assembly may also include a catheter adapter, which may include a catheter and a catheter hub. The second portion of the elongated tubular shaft may be at least partially disposed in the catheter hub.

14 Claims, 4 Drawing Sheets

(56) References Cited

U.S. PATENT DOCUMENTS

| | | | |
|---|---|---|---|
| 9,375,551 | B2 | 6/2016 | Harding |
| 2003/0199827 | A1 | 10/2003 | Thorne |
| 2004/0133124 | A1 | 7/2004 | Bates et al. |

FOREIGN PATENT DOCUMENTS

| | | |
|---|---|---|
| CN | 103906470 | 7/2014 |
| EP | 856330 | 8/1998 |
| EP | 1731190 | 12/2006 |
| JP | 2002320674 | 11/2002 |
| JP | 2005230308 | 9/2005 |
| JP | 2005529717 | 10/2005 |
| WO | 2012/149109 | 11/2012 |

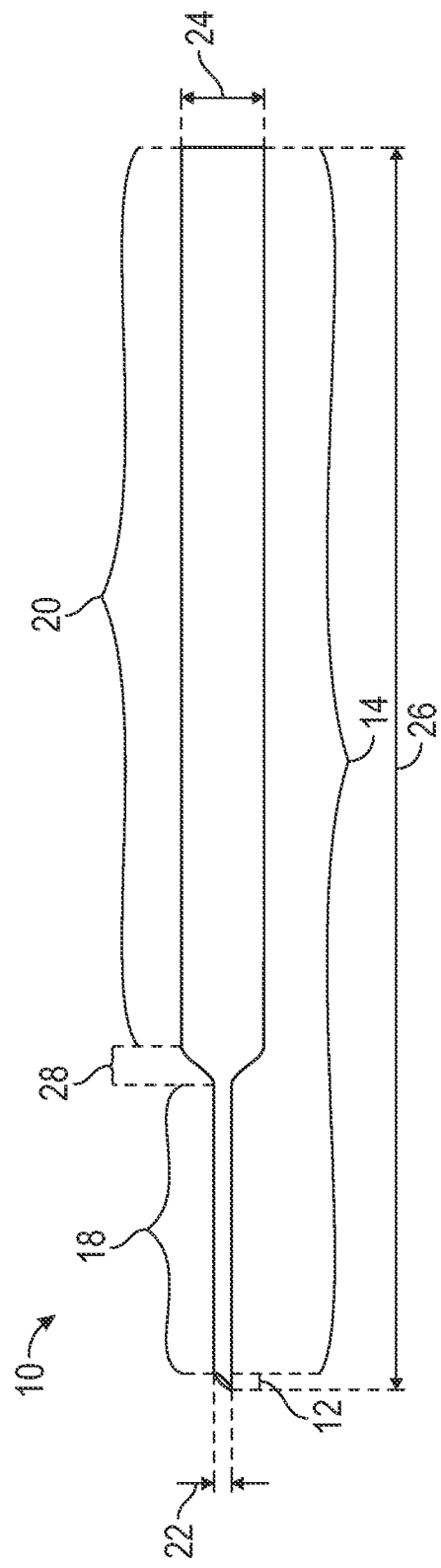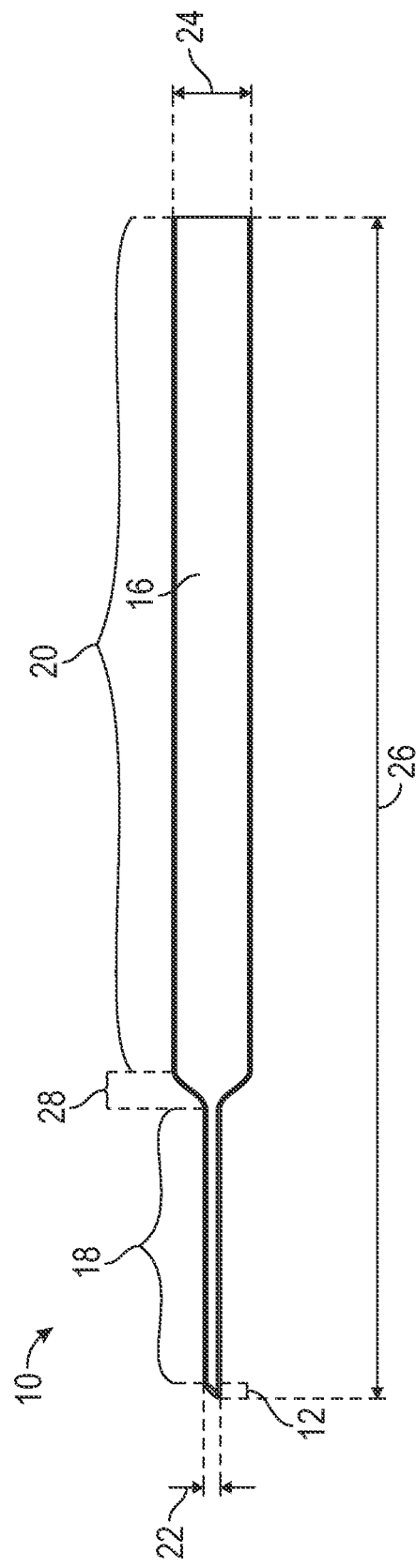

MULTI-DIAMETER CANNULA

RELATED APPLICATIONS

This application is a continuation of U.S. patent application Ser. No. 15/461,363, filed Mar. 16, 2017, and entitled MULTI-DIAMETER CANNULA, which claims the benefit of U.S. Provisional Patent Application No. 62/314,261, filed Mar. 28, 2016, and entitled MULTI-DIAMETER CANNULA, each of which is incorporated herein in its entirety.

BACKGROUND

Needle bending or flexing may occur when a clinician uses a needle insertion device to insert a needle into a patient. For example, in some instances, once the clinician pierces skin of the patient with the needle of the needle insertion device, the clinician may lower an angle of the needle insertion device to place the needle down a vein of the patient, avoiding transfixing the vein. The lowering of the angle of the needle insertion device may cause the needle to flex. The needle flexing may be undesirable for various reasons. For example, the clinician may have difficulty placing the needle in a desired location in the patient due to the needle flexing. As another example, the needle flexing may cause the clinician to alter a needle insertion procedure.

Needle flexing may occur due to a variety of factors, including, for example, one or more of the following: a small outer diameter of the needle, a thin elongated tubular shaft of the needle, a length of the needle, a bevel of a distal tip of the needle, and a safety mechanism that applies a force to the needle. In further detail, while needles with smaller outer diameters may be easier to place in the desired location in a patient, such as, for example, as a vein, the needles with smaller outer diameters may be prone to increased flexing, as opposed to needles with larger outer diameters. Also, longer needles may have various applications, such as, for example, facilitating access to deeper locations within a body of the patient. Longer needles may also be used with longer catheters and/or catheter adapters. However, longer needles may also be prone to increased flexing, as opposed to shorter needles.

Needle flexing may also occur as a result of a tendency of the needle to follow the bevel of the needle when the bevel penetrates the skin and/or tissue of the patient. Furthermore, needle flexing may occur due to a force of a safety clip or mechanism when the needle has a small outer diameter, thin elongated tubular shaft, and/or long length.

Needles with small outer diameters may be easier to place in the desired location in a patient and may be particularly useful for placement in patients who may have damaged veins, such as chemotherapy patients, and/or patients with small veins, such as children. However, needles with small outer diameters may be prone to increased flexing, as described. There is a need in the art for devices, systems, and methods that decrease flexing of the needle and also facilitate placement of the needle.

Such devices, systems, and methods are disclosed herein. In particular, some embodiments described in the present disclosure may relate to a cannula that has a relatively small outer diameter at a distal portion of the cannula, and a relatively large outer diameter at a portion of the cannula proximal to the distal portion. The relatively small outer diameter may facilitate placement of the cannula within the desired location of the patient, such as, for example, a vein, while the relatively large outer diameter may stiffen the cannula and decrease flexing of the cannula.

BRIEF SUMMARY

The present disclosure relates to a multi-diameter cannula. In particular, the present disclosure relates to devices, systems, and associated methods that include a cannula having an elongated tubular shaft with multiple outer diameters, which may facilitate placement of the cannula while providing stiffening of the cannula. For example, the cannula may have an elongated shaft that includes a first portion and a second portion. In some embodiments, the first portion of the elongated tubular shaft may have a first outer diameter. In some embodiments, the first portion may be proximate a distal tip of the cannula. In some embodiments, the second portion of the elongated tubular shaft may have a second outer diameter. In some embodiments, the second outer diameter may be greater than the first outer diameter. The term "multi-diameter cannula" as referred to in the present disclosure, may refer to a cannula that includes an elongated tubular shaft with two, three, four, or more outer diameters.

A length of the first portion may vary. In some embodiments, the first portion may include at least a length of the cannula that is inserted into the vein of a patient. The first outer diameter of the first portion may be small with respect to the second outer diameter and may facilitate placement of the cannula within the vein of the patient, for example. In some embodiments, the first portion may include between three percent and ninety percent of the length of the cannula.

A length of the second portion may vary as well. For example, the second portion may include more than ten percent of the length of the cannula. As another example, the second portion may include between ten percent and ninety five percent of the length of the cannula. As a further example, the second portion may include between forty and sixty percent of the length of the cannula. As yet another example, the second portion may include more than fifty percent of the length of the cannula. The second outer diameter of the second portion may be larger with respect to the first outer diameter and may stiffen the cannula. In some embodiments, the second portion may include an entire length of the cannula that is not inserted in the vein of the patient.

The cannula may be used with any suitable system or device. In one example, the cannula may be used with any suitable catheter assembly, including an over-the-needle peripheral IV catheter assembly. In some embodiments, the cannula may include a hypodermic needle such as, for example, an introducer needle. In some embodiments, the catheter assembly may include an intravenous device, such as, for example, an IV catheter or a PIVC catheter. In some embodiments, the intravenous device may include any intravenous device that includes a cannula. Example intravenous devices may include both straight and ported intravenous catheters such as the AUTOGUARD™ shielded catheter commercially available from Becton, Dickinson, and Company, integrated peripheral intravenous catheters, winged needle sets, blood collection sets, an IV access set such as the BD NEXIVA™ Closed Intravenous (IV) Catheter system available from Becton, Dickinson, and Company, etc. In some embodiments, a catheter assembly may include one or more of the following: the cannula, a catheter adapter, and a cannula shield. In some embodiments, the catheter adapter may include a catheter and/or a catheter hub. In some embodiments, the second portion may be at least partially disposed within the catheter hub. In some embodiments, the second portion may be coupled with the cannula shield. In some embodiments, the first portion may be at least partially disposed within the catheter.

In some embodiments, a distal end of the second portion may be disposed within the catheter hub. In some embodiments, a proximal end of the first portion may be disposed within the catheter hub. In some embodiments, the distal end of the second portion may be disposed within the catheter. In some embodiments, the proximal end of the first portion may be disposed within the catheter. In some embodiments, the first portion may be proximate the second portion. In some embodiments, a third portion may be disposed between the first and second portions. In some embodiments, the third portion may be tapered.

The first outer diameter and the second outer diameter may vary. The first outer diameter may correspond to an outer diameter of a needle with any gauge size. The second outer diameter may correspond to an outer diameter of a needle with any gauge size larger than the first outer diameter. In some embodiments, the first outer diameter may correspond to an outer diameter of a 14 gauge needle, a 28 gauge needle, or a needle with a gauge size in between a 14 gauge needle and a 28 gauge needle. In some embodiments, the first outer diameter may correspond to an outer diameter of, for example, a 22 or 24 gauge needle. In some embodiments, the second outer diameter may correspond to an outer diameter of, for example, an 18 gauge needle. The second outer diameter may be greater than the first outer diameter by various amounts. For example, the second outer diameter may be at least three gauge sizes larger than the first outer diameter, which may provide increased rigidity and stiffness with respect to the cannula and/or provide a cannula capture mechanism. In some embodiments, a difference in the first outer diameter and the second outer diameter may provide an engageable feature that may be engageable with any suitable cannula capture mechanism.

For example, the cannula capture mechanism may include a distal mating component and/or a proximal mating component. In some embodiments, the engageable feature may contact the distal mating component and/or the proximal mating component, which may limit movement of the cannula once the cannula has been moved to a shielded position within, for example, a catheter hub. For example, the distal mating component may include a biased structure, which may be any suitable structure that presses towards the cannula. Accordingly, when the engageable feature is moved proximally past the distal mating component, the distal mating component may move to a position that blocks the engageable feature and prevents the engageable feature from moving proximally past the distal mating component.

In some embodiments, the cannula may be integrally formed in a single piece. In some embodiments, the first portion and the second portion may be separate elements that may be coupled together in any number of ways. For example, the first portion and the second portion may be welded together. As another example, the first and second portion may be coupled together using adhesive. As a further example, the first portion may be inserted into the second portion and coupled with the second portion in an interference fit. The interference fit may be accomplished in any number of ways, such as, for example, mechanical force, crimping, etc. In some embodiments, the interference fit may be accomplished by heating the second portion so the second portion slightly expands, inserting the first portion in the second portion, and allowing the second portion to cool, securing the first portion within the second portion.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIG. 2A is a side view of another multi-diameter cannula, according to some embodiments;

FIG. 2B is a cross-sectional view of the multi-diameter cannula of FIG. 2A, according to some embodiments;

DETAILED DESCRIPTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the cannula locator device, cannula locator system, and associated methods, as represented in FIGS. 1 through 6, is not intended to limit the scope of the invention, as claimed, but is merely representative of some embodiments of the invention.

Figure 1A:
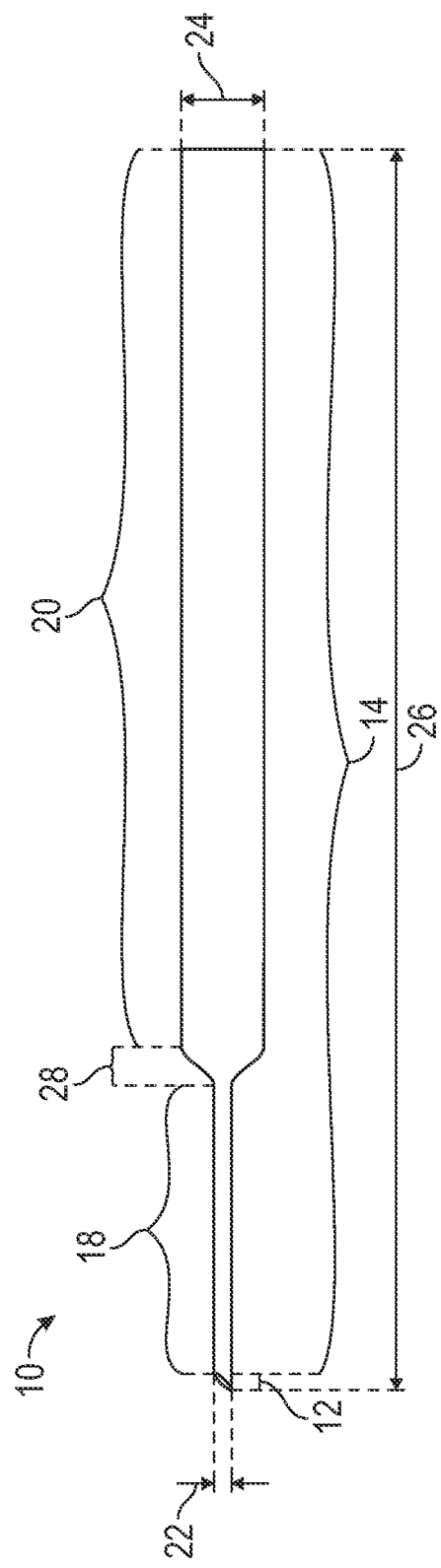
FIG. 1A is a side view of an example multi-diameter cannula, according to some embodiments.
Figure 1B:
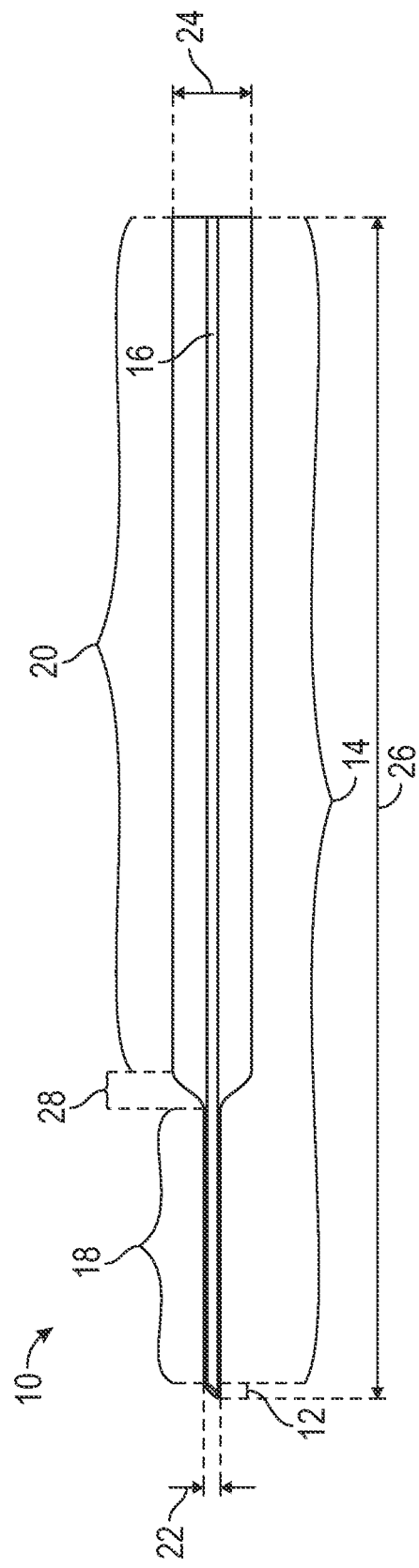
FIG. 1B is a cross-sectional view of the multi-diameter cannula of FIG. 1, according to some embodiments.

Generally, this application relates to a multi-diameter cannula. In particular, the present disclosure relates to devices, systems, and associated methods that include a cannula having an elongated tubular shaft with multiple outer diameters, which may facilitate placement of the cannula while providing stiffening of the cannula. Referring now to FIGS. 1A-1B, in some embodiments, a cannula 10 may include a distal tip 12, an elongated tubular shaft 14, and an inner lumen 16. In some embodiments, the elongated tubular shaft 14 may include a first portion 18 and a second portion 20.

In some embodiments, the first portion 18 of the elongated tubular shaft 14 may have a first outer diameter 22. In some embodiments, the first portion 18 may be proximate the distal tip 12 of the cannula 10. In some embodiments, the second portion 20 of the elongated tubular shaft 14 may have a second outer diameter 24. In some embodiments, the second outer diameter 24 may be greater than the first outer diameter 22, which may stiffen the cannula 10.

A length of the first portion 18 may vary. In some embodiments, the first portion 18 may include at least a length 26 of the cannula 10 that is inserted into the vein of the patient. The first outer diameter 22 of the first portion 18 may be small with respect to the second outer diameter 24 and may facilitate placement of the cannula 10 within the vein of the patient. In some embodiments, the first portion may include between three percent and ninety percent of the length 26 of the cannula 10. In some embodiments, the first portion may include between forty percent and fifty percent of the length 26 of the cannula 10.

A length of the second portion 20 may vary based on, for example, a desired stiffness and/or an interior width of a particular needle insertion device. For example, the second portion 20 may include more than ten percent of the length 26 of the cannula 10. As another example, the second portion 20 may include between ten percent and ninety five percent of the length 26 of the cannula 10. As a further example, the second portion 20 may include between forty and sixty percent of the length 26 of the cannula 10. As yet another example, the second portion 20 may include more than fifty percent of the length 26 of the cannula 10. In some embodiments, the length of the second portion 20 may correspond to between one or more of the following: five and twenty five percent of the length 26 of the cannula 10, twenty five and fifty percent of the length 26 of the cannula 10, fifty percent and seventy five percent of the length 26 of the cannula 10, and seventy five percent and ninety five percent of the length 26 of the cannula 10.

In some embodiments, the first outer diameter 22 may correspond to an outer diameter of, for example, a 22 or 24 gauge needle or another relatively small gauge needle, which may have a particular need for strengthening. In some embodiments, the second outer diameter 24 may correspond to an outer diameter of, for example, an 18 gauge needle. The second outer diameter 24 may be greater than the first outer diameter 22 by various amounts. For example, the second outer diameter 24 may be at least three gauge sizes larger than the first outer diameter 22, which may provide increased rigidity and stiffness with respect to the cannula and/or provide a cannula capture mechanism, as will be explained further with respect to FIGS. 6A-6B.

In some embodiments, the first portion 18 may be proximate the second portion 20. In these embodiments, an intersection of the first portion 18 and the second portion 20 may be stepped. In other embodiments, a third portion 28 may be disposed between the first and second portions 18, 20. In some embodiments, the third portion 28 may be tapered.

As illustrated in FIG. 1B, in some embodiments, a diameter of the inner lumen 16 may be constant. As illustrated in FIG. 2B, in some embodiments, the diameter of the inner lumen may vary with respect to an outer diameter of a cannula 29. In some embodiments, the cannula 29 may correspond to the cannula 10 of FIGS. 1A-1B.

Figure 3:
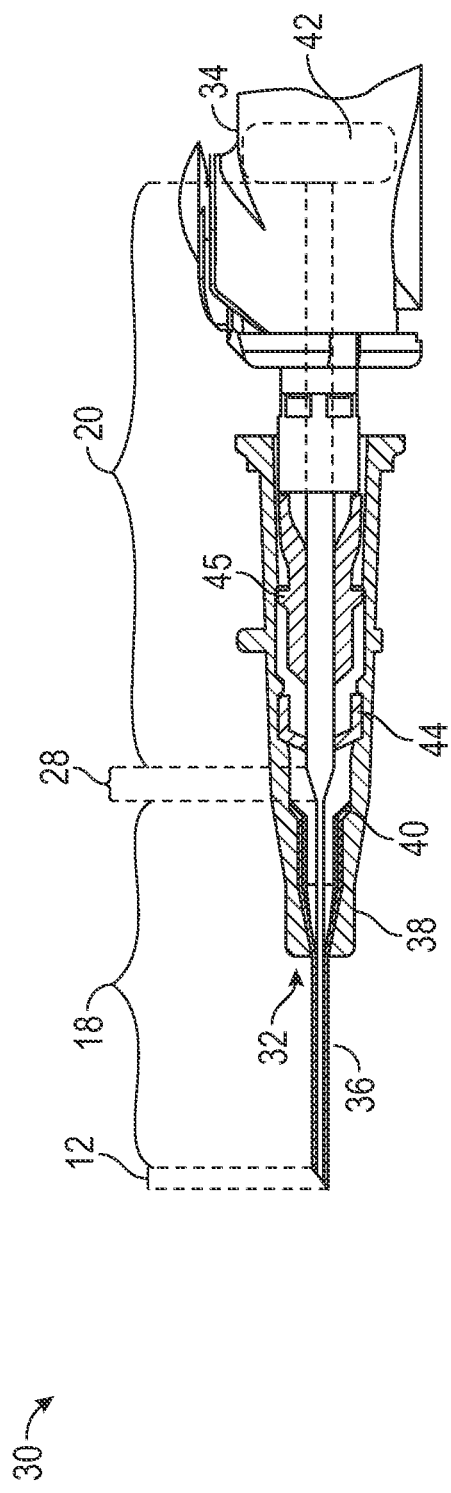
FIG. 3 is a partial cross-sectional view of another example multi-diameter cannula coupled with an example catheter device, according to some embodiments.

Referring now to FIG. 3, in some embodiments, a catheter assembly 30 may include one or more of the following: a cannula 31, a catheter adapter 32, and a cannula shield 34. In some embodiments, the catheter adapter 32 may include one or more of the following: a catheter 36, a catheter hub 38, and a wedge 40. The cannula 31 may be used with any suitable system or device. In one example, the cannula 31 may be used with any suitable catheter assembly, including an over-the-needle peripheral IV catheter assembly. In some embodiments, the cannula 31 may correspond to the cannula 10 of FIGS. 1A-1B and/or the cannula 29 of FIGS. 2A-2B.

In some embodiments, the second portion 20 may be at least partially disposed within the catheter hub 38. In some embodiments, the second portion 20 may be coupled with the cannula shield 34. In some embodiments, the first portion 18 may be at least partially disposed within the catheter. In some embodiments, a first outer diameter 22 of the cannula 31 may be approximately a same size as an inner diameter of at least a distal portion of the catheter 36 such that the cannula 31 and the catheter 36 are engaged in an interference fit.

In some embodiments, a distal end of the second portion 20 may be disposed within the catheter hub 38 and/or a proximal end of the second portion 20 may be disposed within the cannula shield 34. In some embodiments, the proximal end of the second portion 20 may be coupled with a spring 42 or another cannula shielding or safety mechanism. In some embodiments, a proximal end of the first portion may be disposed within the catheter hub proximal to the catheter 36 and/or the wedge 40.

In some embodiments, the cannula shield 34 may be configured to trap the distal tip 12 of the cannula 31 and prevent accidental needle sticks. In some embodiments, the second portion 20 may be configured to move proximally within the cannula shield 34 and the distal tip 12 may be configured to be retracted into the cannula shield 34. In some embodiments, all or a portion of the cannula 31 may be retracted into the cannula shield 34.

In some embodiments, the catheter assembly 30 may include a septum 44 and/or a septum actuator 45. In some embodiments, the second portion 20 may extend through the septum 44 and/or the septum actuator 45 when the cannula is in the unshielded position, as illustrated in FIG. 3.

Figure 4:
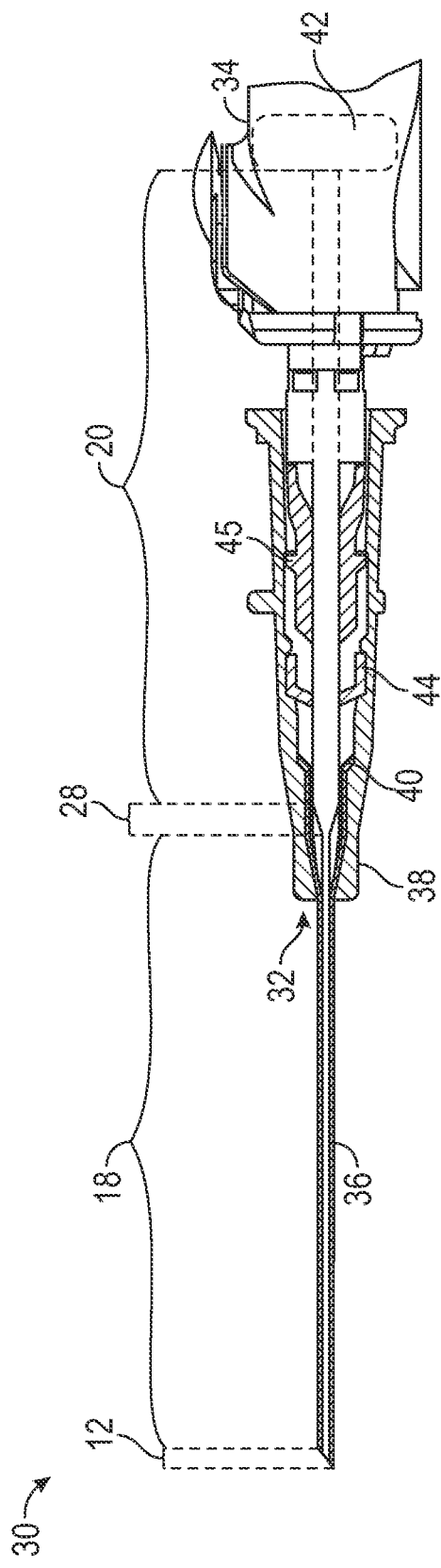
FIG. 4 is a partial cross-sectional view of another example multi-diameter cannula coupled with the catheter device of FIG. 3.

Referring now to FIG. 4, in some embodiments, the distal end of the second portion 20 of a cannula 46 may be disposed within the catheter 36 and/or the wedge 40. In some embodiments, the proximal end of the first portion 18 may be disposed within the catheter 36 and/or the wedge 40. In some embodiments, the cannula 46 may correspond to one or more of the following: the cannula 10 of FIGS. 1A-1B, the cannula 29 of FIGS. 2A-2B, and the cannula 31 of FIG. 3.

In some embodiments, all or a portion of the second portion 20 of the cannula 46 may have an outer diameter that is slightly less than an inner diameter of the catheter hub 38 such that the second portion 20 and the inner diameter of the catheter hub 38 are in close proximity and/or the second portion 20 is slidably movable within the catheter hub 38. In some embodiments, all or a portion of the second portion 20 of the cannula 46 may have an outer diameter that is slightly less than an inner diameter of the wedge 40 such that the second portion 20 and the inner diameter of the wedge 40 are in close proximity and/or the second portion 20 is slidably movable within the wedge 40. The similar diameters of the second portion 20 and the catheter hub 38 and/or the wedge 40 may prevent excess lateral movement of the cannula 46 within the catheter hub 38 and/or the wedge 40.

Figure 5A:
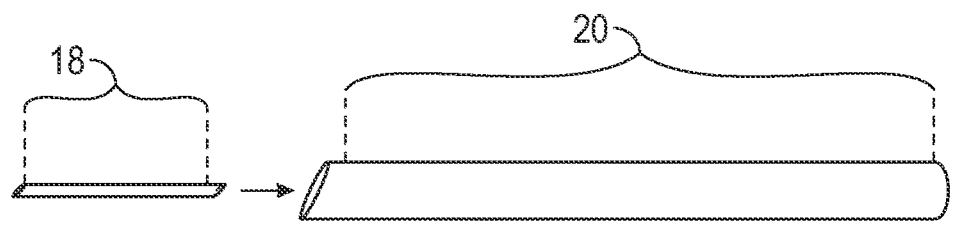
FIG. 5A is a perspective view of a first portion and a second portion of an elongated tubular shaft.
Figure 5B:
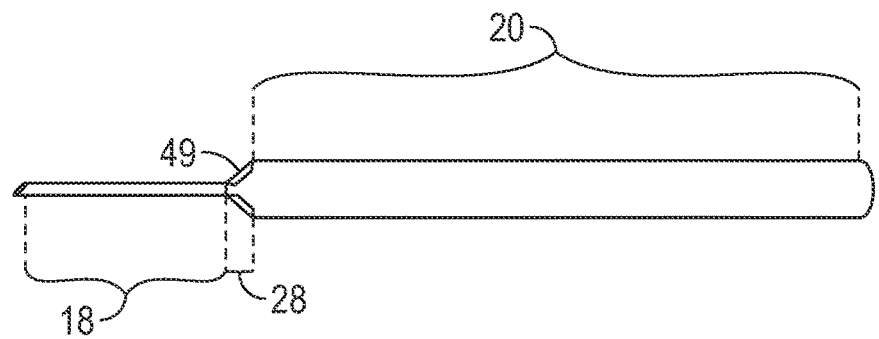
FIG. 5B is a perspective view of the first portion and the second portion of FIG. 5A coupled together.

Referring now to FIGS. 5A-5B, in some embodiments, the first portion 18 and the second portion 20 of a particular cannula may be separate elements that may be coupled together in any number of ways. For example, the first portion 18 and the second portion 20 may be welded together. As another example, the first portion 18 and second portion 20 may be coupled together using adhesive. As a further example, the first portion 18 may be inserted into the second portion 20 and coupled with the second portion 20 in an interference fit, as illustrated in FIG. 5B. The interference fit may be accomplished in any number of ways, such as, for example, mechanical force, crimping, etc. FIG. 5B illustrates an example crimp 49, which may result from crimping the first portion 18 and the second portion 20 together. In some embodiments, the crimp 49 may form the third portion 28 of FIGS. 1-4. In some embodiments, the interference fit may be accomplished by heating the second portion 20 so the second portion 20 slightly expands, inserting the first portion 18 into the second portion 20, and allowing the second portion 20 to cool, securing the first portion 18 within the second portion 20. In some embodiments, the particular cannula may correspond to one or more of the following: the cannula 10 of FIGS. 1A-1B, the cannula 29 of FIGS. 2A-2B, the cannula 31 of FIG. 3, and the cannula 46 of FIG. 4. In some embodiments, a particular cannula may be integrally formed in a single piece.

Figure 6A:
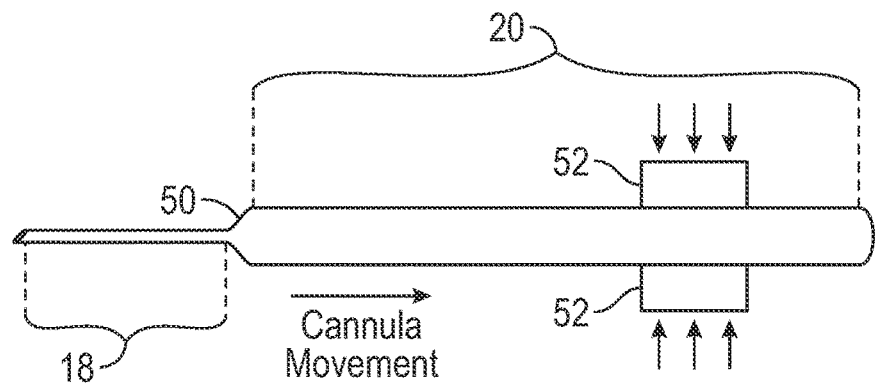
FIG. 6A is a perspective view of the multi-diameter cannula of FIG. 1 coupled with an example distal mating component in an unshielded position.
Figure 6B:
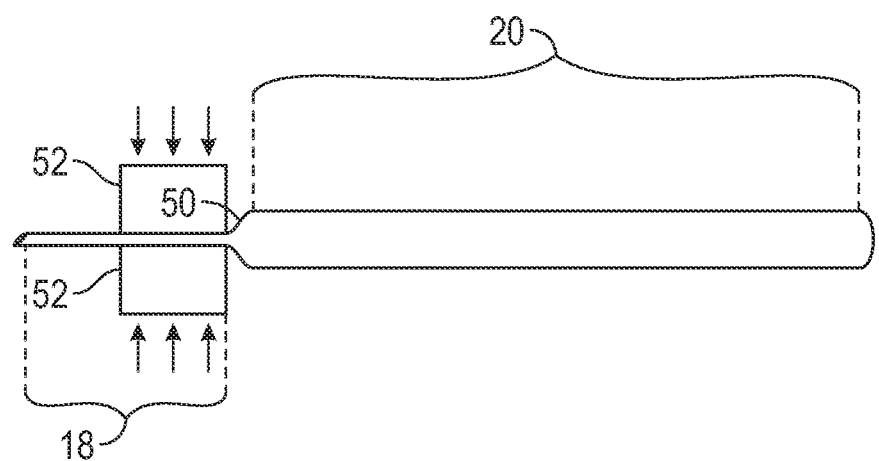
FIG. 6B is a perspective view of the multi-diameter cannula of FIG. 1 coupled with the distal mating component in a shielded position.

Referring now to FIGS. 6A-6B, in some embodiments, a difference between the first outer diameter 22 and the second outer diameter 24 may provide an engageable feature 50 that may be engageable with any suitable cannula capture mechanism. In some embodiments, the engageable feature 50 may include or correspond to the third portion 28 of FIGS. 1-5. In some embodiments, the engageable feature 50 may include a notch feature, a welded ferrule feature, a crimp feature, or another suitable engageable cannula feature.

For example, the cannula capture mechanism may include a distal mating component and/or a proximal mating component. In some embodiments, the engageable feature 50 may contact the distal mating component and/or the proximal mating component, which may limit movement of the cannula 10 once the cannula has been moved to a shielded position within, for example, a catheter hub. For example, the distal mating component may include a biased structure 52, which may be any suitable structure that presses towards the cannula 10. Accordingly, when the engageable feature 50 is moved proximally past the distal mating component, the distal mating component may move to a position that blocks the engageable feature 50 and prevents the engageable feature 50 from moving proximally past the distal mating component. In some embodiments, the catheter assembly 30, illustrated in FIGS. 3 and 4, may include the engageable feature 50.

In addition to the previously described embodiments of the multi-diameter cannula, the multi-diameter cannula, including one or more of the cannula 10 of FIGS. 1A-1B, the cannula 29 of FIGS. 2A-2B, the cannula 31 of FIG. 3, and the cannula 46 of FIG. 4, may be modified in any suitable manner that allows it to fulfill its intended purpose. For example, the multi-diameter cannula may include three, four, five, six, or more portions each having a constant outer diameter. In these and other embodiments, the multi-diameter cannula may include a combination of constant outer diameter portions and variable outer diameter portions. As another example, the multi-diameter cannula may include an outer diameter that is variable along an entire length of the multi-diameter cannula. The number of diameters of the cannula may be determined, for example, based on an internal geometry of a needle insertion device, such as a catheter assembly.

Further, the multi-diameter cannula may be used in any suitable manner. For example, the multi-diameter cannula may be used during various medical procedures, such as, for example, an intravenous infusion, blood draw, spinal tap, or epidural. The multi-diameter cannula may be used with any number of cannula safety mechanisms. For example, the multi-diameter cannula may move through a cannula shield of a particular catheter device and a distal tip of multi-diameter cannula may be trapped within the cannula shield. In some embodiments, the cannula shield may be coupled with the catheter adapter. As another example, the multi-diameter cannula may be used with a unitary or multiple piece clip. The clip may, for example, be slideable from a first position in which the multi-diameter cannula is exposed to a second position in which the distal tip of the multi-diameter cannula is covered or shielded, rendering the cannula protected. A particular cannula safety mechanism may be disposed internally within the catheter adapter and/or may be disposed externally to the catheter adapter.

Also, in addition to the previously described embodiments of the catheter assembly 30, the catheter assembly 30 may be modified in any suitable manner that allows it to fulfill its intended purpose.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
   a catheter adapter comprising a distal end, a proximal end, and an inner lumen extending therebetween;
   a catheter coupled to the distal end of the catheter adapter;
   a cannula shield coupled to the proximal end of the catheter adapter; and
   an introducer needle extending distally from the cannula shield and through the catheter, wherein the introducer needle comprises a sharp distal tip and a stepped or tapered surface, wherein the introducer needle comprises a first outer diameter extending from the sharp distal tip to the stepped or tapered surface and a second outer diameter extending from the stepped or tapered surface to the cannula shield.

2. The catheter assembly of claim 1, further comprising a cannula having a sharp distal tip, wherein the cannula is configured to move proximally within the cannula shield and the sharp distal tip of the cannula is configured to be retracted into the cannula shield.

3. The catheter assembly of claim 1, wherein the second outer diameter is at least three gauge sizes larger than the first outer diameter.

4. The catheter assembly of claim 1, wherein the first outer diameter corresponds to an outer diameter of a 14 gauge needle, a 28 gauge needle, or a needle with a gauge size in between a 14 gauge needle and a 28 gauge needle.

5. The catheter assembly of claim 1, further comprising a septum disposed within the inner lumen of the catheter adapter, wherein the second outer diameter extends through the septum.

6. The catheter assembly of claim 1, wherein the stepped or tapered surface is disposed within the catheter adapter.

7. The catheter assembly of claim 6, wherein the stepped or tapered surface is disposed within the catheter.

8. The catheter assembly of claim 7, further comprising a wedge disposed within an inner surface of the catheter adapter, wherein the stepped or tapered surface is disposed within the wedge.

9. The catheter assembly of claim 1, further comprising a septum actuator disposed within the inner lumen of the catheter adapter, wherein the second outer diameter extends through the septum actuator.

10. The catheter assembly of claim 1, wherein the stepped or tapered surface is stepped.

11. The catheter assembly of claim 1, wherein the stepped or tapered surface is tapered.

12. The catheter assembly of claim 1, wherein the introducer needle comprises: a first portion comprising the first outer diameter extending from the sharp distal tip to the stepped or tapered surface; and a second portion comprising the second outer diameter extending from the stepped or tapered surface to the cannula shield, wherein the first portion and the second portion are coupled together via a crimp disposed on the stepped or tapered surface.

13. A method, comprising:
   forming the introducer needle of claim 1, wherein the introducer needle comprises:
      a first portion comprising the first outer diameter extending from the sharp distal tip to the stepped or tapered surface; and
      a second portion comprising the second outer diameter extending from the stepped or tapered surface to the cannula shield, wherein forming the introducer needle comprises coupling the first portion to the second portion.

14. The method of claim 13, wherein the first portion is coupled to the second portion by welding, adhesive, or an interference fit.

* * * * *